(12) United States Patent
Liu et al.

(10) Patent No.: US 7,442,834 B2
(45) Date of Patent: Oct. 28, 2008

(54) PROCESS SUITABLE FOR INDUSTRIAL SCALE PRODUCTION OF GABAPENTIN

(75) Inventors: Tianchun Liu, Hangzhou (CN);
Youming Huang, Hangzhou (CN);
Weirong Fan, Hangzhou (CN)

(73) Assignee: Zhejiang Chiral Medicine Chemicals Co., Ltd., Hangzhou (CN)

( * ) Notice: Subject to any disclaimer, the term of this patent is extended or adjusted under 35 U.S.C. 154(b) by 17 days.

(21) Appl. No.: 11/457,023

(22) Filed: Jul. 12, 2006

(65) Prior Publication Data

US 2007/0287861 A1  Dec. 13, 2007

(51) Int. Cl.
*C07C 229/00* (2006.01)

(52) U.S. Cl. .................................... 562/507

(58) Field of Classification Search ........ None
See application file for complete search history.

(56) References Cited

U.S. PATENT DOCUMENTS

| | | | |
|---|---|---|---|
| 4,024,175 A | 5/1977 | Satzinger et al. | 560/122 |
| 4,087,544 A | 5/1978 | Satzinger et al. | 514/530 |
| 5,091,567 A | 2/1992 | Geibel et al. | 562/507 |
| 5,319,135 A | 6/1994 | Jennings et al. | 562/507 |
| 6,054,482 A | 4/2000 | Augart et al. | 514/561 |
| 6,518,456 B1 | 2/2003 | Peverali et al. | 562/507 |
| 7,199,266 B2 | 4/2007 | Cannata et al. | 514/561 |
| 2005/0113582 A1* | 5/2005 | Wenzl et al. | 548/234 |
| 2006/0135789 A1* | 6/2006 | Kuppuswamy et al. | 548/408 |
| 2006/0149099 A1 | 7/2006 | Kuppuswamy et al. | 562/507 |

FOREIGN PATENT DOCUMENTS

| | | |
|---|---|---|
| IN | 186285 | 1/2000 |
| WO | WO 99/14184 | 3/1999 |
| WO | WO 02/34709 | 5/2002 |
| WO | WO 2004/046108 | 6/2004 |

* cited by examiner

*Primary Examiner*—Paul A Zucker
(74) *Attorney, Agent, or Firm*—Fulbright & Jaworski L.L.P.

(57) ABSTRACT

This invention relates to an improved process for the preparation of substantially pure, stable anhydrous gabapentin. Thus, cyclohexane 1,1-diacetic acid monoamide is first treated with NaOH/NaClO to form 3,3-pentamethylenebutyrolactam, which is treated with aqueous HCl solution under reflux to provide gabapentin HCl salt, which is then neutralized with NaOH followed by a dehydration step to provide substantially pure, storage-stable, pharmaceutical grade gabapentin.

31 Claims, No Drawings

PROCESS SUITABLE FOR INDUSTRIAL SCALE PRODUCTION OF GABAPENTIN

FIELD OF THE INVENTION

This invention relates to a chemical process for the production of pharmaceutical grade gabapentin, a very useful therapeutic agent for cerebral disorders with extremely low toxicity in human.

Benefit of priority to Chinese Applications 200610051909.5 and 200610051910.8, both filed Jun. 12, 2006, is claimed, and the contents of these applications are hereby incorporated by reference in their entirety.

BACKGROUND OF THE INVENTION

Gabapentin, a generic name for 1-(aminomethyl)-1-cyclohexaneacetic acid (I), first disclosed in U.S. Pat. No. 4,024,175 by Warner-Lambert Co., is a very useful therapeutic agent for cerebral disorders with extremely low toxicity in human.

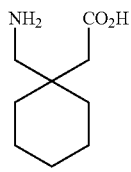

I

There are a number of patented processes for manufacturing this compound. Typical processes are exemplified by U.S. Pat. Nos. 4,024,175, 6,518,456, WO02/34709, WO2004046108, Indian patent 186285, U.S. Pat. Nos. 5,319,135, 5,091,567, and WO 9914184.

U.S. Pat. Nos. 4,024,175 and 4,087,544 disclosed that 1-aminomethyl-1-cyclopentane-acetic acid hydrochloride can be prepared by treating 1,1-cyclopentane-diacetic acid monoamide with NaOH/NaBrO followed by HCl. 1,1-cyclopentane-diacetic acid monoamide hydrochloride was obtained by passing the gabapentin HCl salt through an anion exchange column. However, no yield and purity was reported in these patents. Following similar procedures, except with a cation exchange resin for the last step, WO 02/34709 disclosed a method for the preparation of gabapentin with as much as 80% yield. However, the purity of the product again was not disclosed. These methods require a large amount of solvents for the ion exchange process.

Scheme 1

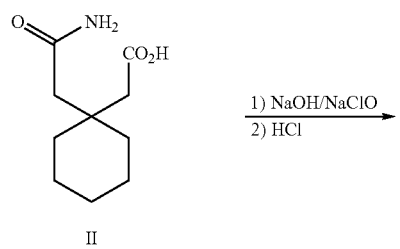

A very useful improvement on the process of converting gabapentin HCl salt into gabapentin was disclosed in U.S. Pat. No. 6,518,456, in which gabapentin HCl salt was neutralized with a base, such as NaOH, to the isoelectric point of gabapentin, i.e., pH=7.1-7.2, thus allowing the precipitation and isolation monohydrate via filtration of crude gabapentin monohydrate (Ia) (Scheme 2). The crude gabapentin monohydrate can then be converted to gabapentin in alcohol/ether mixture. This process represents a major advancement for the isolation of gabapentin, avoiding the solvent-consuming ion exchange column chromatography method, although it needed very careful control of the amount and rate of the base added so that the pH of the solution would not fall out of the narrow range of 7.1-7.2.

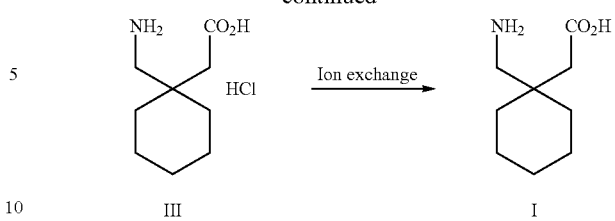

Scheme 2

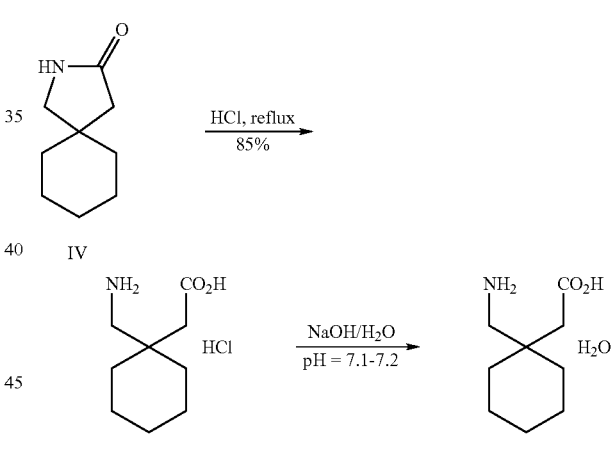

In Indian patent 186,285, cyclohexane 1,1-diacetic acid monoamide (II) was converted into 3,3-pentamethylenebutyrolactam (IV) through the treatment with NaOH/Br$_2$, although no yield or purity of the lactam was reported. Subsequently, the lactam IV was converted to gabapentin HCl salt (III), which was turned into gabapentin (I) by slowly neutralizing gabapentin HCl salt (III) with NaOH solution to pH between 7.4-7.8 (Scheme 3) for the isolation of gabapentin (I). The neutralization process needed to be very well controlled and took about 6 hours. WO 2004046108 disclosed an improved process for the first step, reaching a yield as high as 82%. These processes use bromine, a very corrosive chemical, which erodes manufacturing facilities and releases harmful fumes into the working environment, and thus not ideal for industrial scale application.

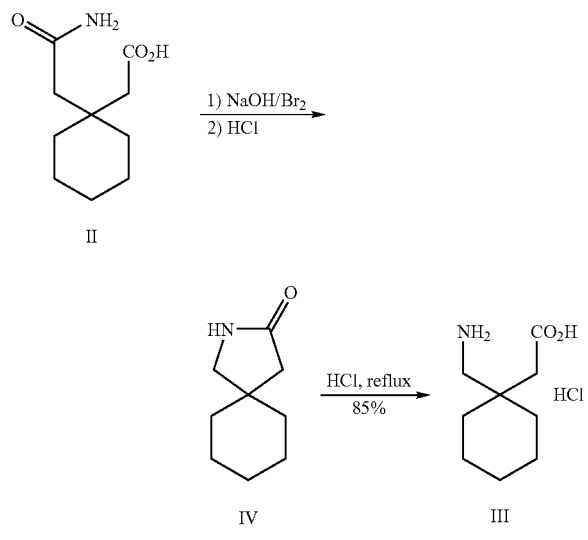

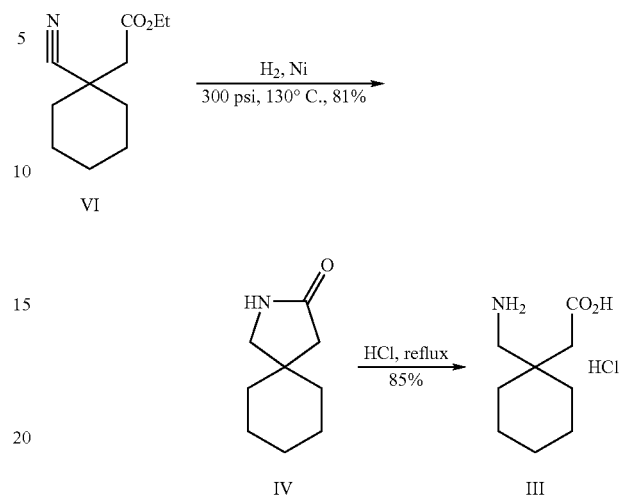

Other processes, exemplified by U.S. Pat. No. 5,091,567, WO 9914184 (Scheme 4), and U.S. Pat. No. 5,319,153 (Scheme 5), require catalytic hydrogenation of intermediates at elevated pressure and sometimes elevated temperatures.

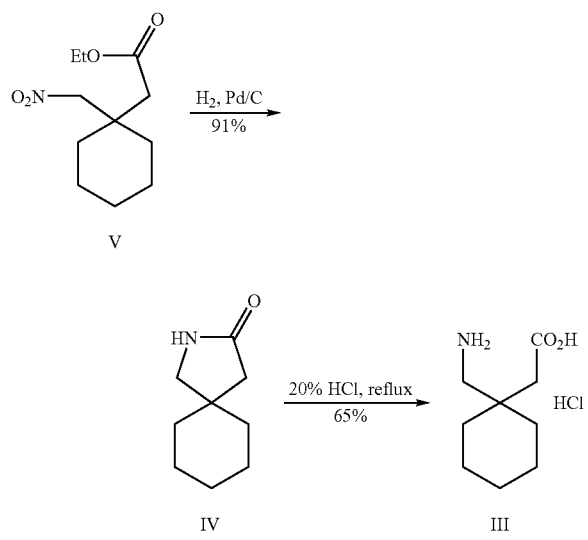

Thus, there remains a need for new and improved methods of manufacturing gabapentin (I) from, e.g., cyclohexane 1,1-diacetic acid monoamide (II), a mass produced feed stock that is mass produced.

It has been shown that of 3,3-pentamethylenebutyrolactam (IV) can be formed during storage of gabapentin (I) for unknown reasons. The cytotoxicity of IV ($LD_{50}$=300 mg/kg) is much higher than that of gabapentin (I) ($LD_{50}$>8000 mg/Kg) [U.S. Pat. No. 6,054,482]. Therefore, not only the initial content of IV must be controlled at less than 0.5%, but also the formation of IV from gabapentin (I) must be minimized for safety reason. Thus, another needed improvement is to manufacture stable gabapentin (I) under storage conditions. The formation of 3,3-pentamethylenebutyrolactam (IV) is a competing side reaction during the neutralization of gabapentin HCl salt (III) as well as during the dehydration process of gabapentin hydrate. Thus, yet another needed improvemetn is to recover as much 3,3-pentamethylenebutyrolactam (IV) as possible to reduce the loss of useful intermediates and increase the yield of the final product.

SUMMARY OF THE INVENTION

This invention covers an improved process for the preparation of highly pure, stable, anhydrous gabapentin (I) from cyclohexane 1,1-diacetic acid monoamide (II).

The first aspect of the invention is concerned with a high yielding process for the preparation of 3,3-pentamethylenebutyrolactam (IV) from cyclohexane 1,1-diacetic acid monoamide (II) and hypochlorite in water under basic conditions (step a). The product, IV, is produced in high yield after most of the base has been neutralized with an acid and can be easily separated in pure form from the impurities by either filtration or extracting the crude product with an organic solvent or combination of organic solvents.

Step A

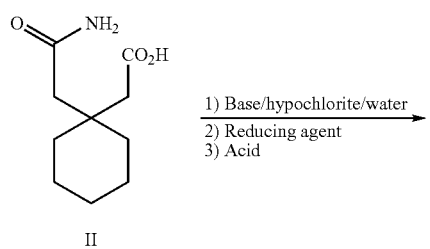

The second step of the invention is concerned with converting 3,3-pentamethylenebutyrolactam (IV) to a gabapentin salt (III) under acidic conditions in water (step b). The unreacted IV may be removed by extraction with an organic solvent or combination of organic solvents and recycled.

Step B

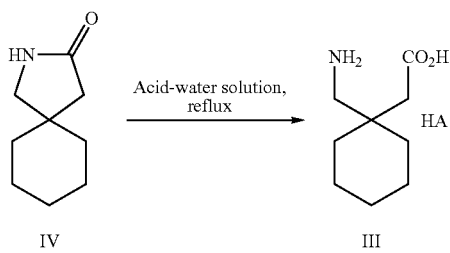

The third step of the invention is concerned with treating gabapentin salt with a base to raise the pH to 8.0-8.5 in a water—$C_1$—$C_4$ alcohol solution to allow the precipitation and isolation of gabapentin hydrate (Ia) (step c). The base used may be any of the inorganic bases such as NaOH, KOH, $Na_2CO_3$, $K_2CO_3$, $NaHCO_3$, and $KHCO_3$, or combinations thereof.

Step C

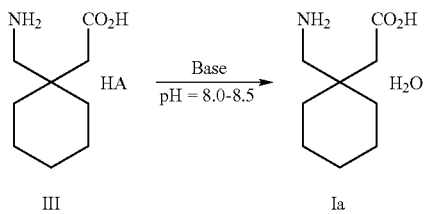

The last step of the invention is concerned with converting gabapentin hydrate (Ia) to the corresponding pharmaceutical grade anhydrous form (I) (step d) by subjecting gabapentin hydrate (Ia) to an aqueous-alcoholic solution.

Step D

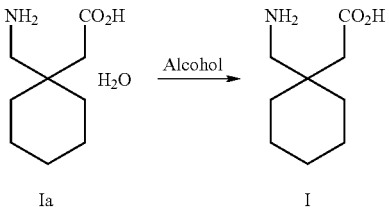

DETAILED DESCRIPTION OF THE INVENTION

The instant invention is a high yielding for the preparation of highly pure, stable, anhydrous gabapentin (I) from cyclohexane 1,1-diacetic acid monoamide (II).

In step (a), cyclohexane 1,1-diacetic acid monoamide (II) was treated with a base and a hypochlorite in aqueous solution at low temperature first, followed by at slightly elevated temperature to complete the Hofmann rearrangement. The excess amount of hypochlorite is then removed by a reducing agent, preferably $NaHSO_3$. The pH of the reaction mixture is then lowered with an acid, preferably HCl, to 8-9, particularly 8.2-8.8. The mixture was refluxed for a few hours and then cooled. The pH again is adjusted with acid, preferably HCl, to 8.5±0.5, when necessary. The product is extracted with a non-water miscible organic solvent, preferably toluene or dichloromethane. The organic layer is then evaporated to dryness to provide 3,3-pentamethylenebutyrolactam (IV). The Hofmann rearrangement reaction performed under the conditions specified in the instant invention produces compound IV in very high purity with an over 95% yield, representing a significant improvement over Indian patent 186285 and WO 2004/046108A1, where $NaOH/Br_2$ were used to manufacture 3,3-pentamethylenebutyrolactam (IV), but only reached as high as 82% yield.

In step (b), 3,3-pentamethylenebutyrolactam (IV) is treated with an aqueous acid, preferably HCl, at elevated temperature, preferably at reflux temperature, to provide the salt of gabapentin, preferably gabapentin HCl salt. Because of the poor solubility of gabapentin salt, the residual 3,3-pentamethylenebutyrolactam (IV) can be easily removed from the reaction mixture by extraction with a water immiscible organic solvent, preferably toluene and dichloromethane. The gabapentin salt can then be precipitated at low temperature, preferably at 0-5° C. The acidic mother liquor can be used to neutralize base in the previous step or its concentration can be raised by adding fresh, more concentrated acid and reused in this step.

In step (c), gabapentin salt (III) is mixed with water and the pH of the solution is raised to 4.5-5.0 with a base to dissolve the solid, while the temperature is maintained at 20-30° C. Activated carbon was used to discolor the solution. After the activated carbon is removed by filtration, an alcohol is added to the filtrate and the temperature was lowered, preferably to 0-10° C. The pH is again raised, preferably to 8.0-8.5, with a base, preferably NaOH solution. The temperature is controlled at 0±2° C. to precipitate gabapentin. The solid product, gabapentin monohydrate, is separated via filtration and washed water and alcohol.

In step (d), gabapentin monohydrate is stirred with a C1-C4 alcohol or alcohol-water mixture, preferably aqueous ethanol solution, most favorably 95% ethanol, at slightly elevated temperature, preferably 30-50° C., for a short period of time, preferably half an hour. Upon cooling, preferably to 0±2° C., and stirring at this temperature for 1 to 5 hours, preferably 1 to 3 hours, most favorably 1 to 2 hours, solid anhydrous gabapentin needles precipitates out and is collected by filtration. A small amount of 3,3-pentamethylenebutyrolactam (IV) formed during this dehydration process stays in the alcoholic mother liquor and can be recovered.

EXAMPLES

The following examples describe the preferred embodiment of the invention and are not intended to limit the scope of the invention. The specification of these examples should only be considered exemplary, with the scope and spirit of the invention being indicated in the claims.

Example 1

3,3-Pentamethylenebutyrolactam (IV)

Water (380 mL), 324 g of NaOH solution (30%) were added to a 2000 mL reaction flask. The solution was cooled to 10-20° C. Cyclohexane 1,1-diacetic acid monoamide (II) (160 g) was added. The mixture was stirred until all solid dissolved, and the cooled to 0-15° C. NaClO solution (557 g, 11.3%) was added dropwise. The temperature was slowly raised to 40-50° C. and stirred at this temperature for 3 h. Sodium bisulfite was added to destroy remaining NaClO. The pH was adjusted to 11 to 12 with 31% aqueous HCl solution. The mixture was refluxed (100-105° C.) for 3 hours and then cooled to 50-60° C. The mixture was extracted with toluene. Toluene layer was evaporated to dryness to afford white crystalline 3,3-pentamethylenebutyrolactam (IV), 118 g, Yield: 95.9%; purity, 99.65% (HPLC).

Example 2

3,3-Pentamethylenebutyrolactam (IV)

Water (420 L) and 420 kg of NaOH solution (30%) were added to a 2000 L reaction vessel. The solution was cooled to 10-20° C. Cyclohexane 1,1-diacetic acid monoamide (II) (160 kg) was added. The mixture was stirred until all solid dissolved, and the cooled to 0-15° C. NaClO solution (630 kg, 11.3%) was added dropwise at 0-5° C. The temperature was slowly raised to 40-50° C. and stirred at this temperature for 3 h. Sodium bisulfite was added to destroy remaining NaClO and starch-KI paper was used to assure that the excess NaClO was all destroyed. The pH was adjusted to 11 to 12 with 30% aqueous HCl solution. The mixture was refluxed for 3 hours and then distilled and 300 to 400 L of water was distilled. The mixture was cooled to 0-5° C. and centrifuged. White crystalline product was obtained after toluene layer was evaporated the product was dried in vacuo, 115.5 kg, yield: 93.8%; purity, 99.7%, mp: 90-92° C.

Example 3

Gabapentin HCl Salt (III)

3,3-Pentamethylenebutyrolactam (IV) (250 g), concentrated HCl (1500 g) and water (300 g) was refluxed for 5 h and cooled to 80-90° C. The mixture was cooled to −5 to 5° C. to precipitate the crude product. The solid was filtered to provide wet gabapentin HCl salt (III), equivalent to 308 g of dry gabapentin HCl salt (the water content was measured with Karl-Fisher method and discounted); yield: 90.9%, purity, 98.5% (HPLC); 3,3-pentamethylenebutyrolactam (IV) content, 0.4%. The HCl concentration of filtrate is about 15-16%, which can be used to neutralize NaOH in the previous step or its HCl concentration can be raised to 22% by adding 36% HCl and reused in this step. 3,3-Pentamethylenebutyrolactam (IV) may also be recovered from this HCl solution (see Example 7).

Example 4

3,3-Pentamethylenebutyrolactam (IV)

Water (380 mL), 324 g of NaOH solution (30%) were added to a 2000 mL reaction flask. The solution was cooled to 10-15° C. Cyclohexane 1,1-diacetic acid monoamide (II) (160 g) was added. The mixture was stirred until all solid dissolved, and the cooled to 0-5° C. NaClO solution (557 g, 11.3%) was added dropwise at 0-5° C. The mixture was further stirred for 1.5 h at 5-10° C. The temperature was slowly raised to 35-40° C. in an hour and stirred at this temperature for 2 h. Sodium bisulfite (2-5 g) was added to destroy remaining NaClO. The pH was adjusted to 8.5±0.3 with HCl solution recycled from the hydrolysis of 3,3-pentamethylenebutyrolactam (IV). The mixture was reflux (100-105° C.) for 3 hours and then cooled to 60-65° C. The pH again was adjusted with 31% HCl to 8.5±0.5. The mixture was extracted with toluene (400 mL×2). Toluene layer was evaporated to dryness, to obtain white crystalline 3,3-pentamethylenebutyrolactam (IV), 129 g, Yield: 104.8% (due to the use of recycled HCl, which contained some 3,3-pentamethylenebutyrolactam (IV), the yield is higher than 100%); purity, 99.9% (HPLC).

Example 5

Gabapentin Monohydrate (Ia)

Purified water (750 mL), gabapentin HCl salt (III) (500 g) were mixed in a 2000 mL flask and stirred for 0.5 h. The pH was adjusted to 4.5-5.0 with 30% NaOH solution while the temperature was maintained at 20-30° C. After the solid all dissolved, the temperature was raised to 25-30° C. Activated carbon (2 g) and silicate (0.5 g) were added and stirred for 0.5 h. The suspension was filtered. Ethanol (95%, 300 mL) was added to the filtrate and the temperature was lowered to 0-5° C. The solid was filtered and washed with water to afford white solid, yield: 85%, purity, 99.5% (HPLC). The content of 3,3-pentamethylenebutyrolactam is less than 0.1%. 3,3-Pentamethylenebutyrolactam (IV) in the filtrate is recovered (see Example 7).

Example 6

Anhydrous Gabapentin

Ethanol (95%, 750 g) was heated to 45° C. while being stirred. Gabapentin (350 g) was added and stirred for 0.5 h at 35-40° C. The temperature was slowly lowered to 0±2° C. and stirred at this temperature for 2 h. The solid was filtered by centrifugation and washed with ice cold 95% ethanol. The wet product was dried. Yield: 95%; purity, 99.8%. 3,3-Pentamethylenebutyrolactam (IV) was not detected and the amount of Cl⁻ was 50 ppm. From the mother liquor, 3,3-pentamethylenebutyrolactam (IV) can be recovered after the alcohol has been distilled off (see Example 7).

10 g were drawn per batch, packed and sealed in double polyethylene bags, kept in cardboard drums, and stored under the following conditions. The analyses were performed at the preset time intervals for purity and impurities.

Conditions:
a) Temperature: 40±2° C.
b) Relative humidity: 75±5%
c) Interval for analysis: 0, 1, 2, 3, and 6 months
d) Total period: 6 months

TABLE 1

Accelerated Stability Data

| Batch Number | Time (month) | Appearance | Water content | Purity (wt %) | Impurities | | |
|---|---|---|---|---|---|---|---|
| | | | | | Compound IV | Other unknown impurities | Total impurities |
| 20041201 | 0 | ✓[a] | 0.03% | 100.96% | ND[b] | 0.05% | 0.05% |
| | 1 | ✓ | 0.02% | 100.01% | ND | 0.06% | 0.06% |
| | 2 | ✓ | 0.02% | 100.30% | ND | 0.05% | 0.05% |
| | 3 | ✓ | 0.03% | 100.41% | ND | 0.05% | 0.05% |
| | 6 | ✓ | 0.03% | 99.99% | ND | 0.06% | 0.06% |
| 20041202 | 0 | ✓ | 0.02% | 101.36% | ND | 0.04% | 0.04% |
| | 1 | ✓ | 0.03% | 100.30% | ND | 0.04% | 0.04% |
| | 2 | ✓ | 0.02% | 100.28% | ND | 0.04% | 0.04% |
| | 3 | ✓ | 0.02% | 101.19% | ND | 0.04% | 0.04% |
| | 6 | ✓ | 0.03% | 100.01% | ND | 0.05% | 0.05% |
| 20041203 | 0 | ✓ | 0.02% | 100.96% | ND | 0.06% | 0.06% |
| | 1 | ✓ | 0.03% | 100.30% | ND | 0.06% | 0.06% |
| | 2 | ✓ | 0.03% | 100.27% | ND | 0.04% | 0.04% |
| | 3 | ✓ | 0.03% | 100.43% | ND | 0.05% | 0.05% |
| | 6 | ✓ | 0.02% | 99.84% | ND | 0.06% | 0.06% |

Note:
[a]The appearance of the sample stayed as white or off-white crystalline powder.
[b]ND = not detected.

The test results showed that there are no apparent changes in the samples under the test conditions for up to six months. Therefore, it can be concluded that our product is stable under the accelerated stability test conditions.

Example 7

Recovery of 3,3-Pentamethylenebutyrolactam (IV)

The pH of the mother liquor obtained from Example 3, 5, or 6 was adjusted with 30% aqueous NaOH solution to 10 to 14. The solution was refluxed for 2 hours. Part of the solvent was removed by distillation. The mixture was cooled to 0 to 5° C. The 3,3-pentamethylenebutyrolactam (IV) was filtered, washed with ice-water, and dried in vacuo. White crystalline product has a purity of 99.5% and can be used directly as starting material for the preparation of gabapentin salt.

Example 8

Accelerated Stability Studies on Gabapentin (I)

Accelerated stability studies were carried out as per ICH guidelines at 40±2° C. and 75±5% relative humidity. Accelerated stability studies were carried out on three consecutive batches of final product, gabapentin (I). Six samples each of

Example 9

Long-Term Stability Studies on Gabapentin (I)

Long term stability studies were carried out as per ICH guidelines at 25±2° C. and 60±5% relative humidity. The results shall be updated with the annual update. Long-term stability studies were carried out on three consecutive commercial batches. Twelve samples each of 10 g were drawn per batch, packed and sealed in double polyethylene bags, kept in cardboard drums, and stored under the following conditions. The analyses were performed at the preset time intervals for purity and impurities.

Conditions:
a) Temperature: 25±2° C.
b) Relative humidity: 65±5%
c) Interval for analysis: 0, 3, 6, 9, 12, 18, 24, 36, and 48 months
d) Total period: 48 months

TABLE 2

Long-term Stability Study Data

| Batch Number | Time (month) | Appearance | Water content | Purity (wt %) | Impurity | | |
|---|---|---|---|---|---|---|---|
| | | | | | Compound IV | Other unknown impurities | Total impurities |
| 20041201 | 0 | ✓[a] | 0.03% | 100.96% | ND[b] | 0.05% | 0.05% |
| | 3 | ✓ | 0.03% | 99.75% | ND | 0.06% | 0.06% |
| | 6 | ✓ | 0.02% | 100.33% | ND | 0.07% | 0.07% |
| | 9 | ✓ | 0.03% | 100.30% | ND | 0.06% | 0.06% |
| | 12 | ✓ | 0.03% | 100.13% | ND | 0.03% | 0.03% |
| 20041202 | 0 | ✓ | 0.02% | 101.36% | ND | 0.04% | 0.04% |
| | 3 | ✓ | 0.03% | 100.08% | ND | 0.04% | 0.04% |
| | 6 | ✓ | 0.02% | 100.64% | ND | 0.05% | 0.05% |
| | 9 | ✓ | 0.02% | 100.41% | ND | 0.04% | 0.04% |
| | 12 | ✓ | 0.03% | 100.00% | ND | 0.02% | 0.02% |
| 20041203 | 0 | ✓ | 0.02% | 100.96% | ND | 0.06% | 0.06% |
| | 3 | ✓ | 0.03% | 99.82% | ND | 0.06% | 0.06% |
| | 6 | ✓ | 0.03% | 100.25% | ND | 0.07% | 0.07% |
| | 9 | ✓ | 0.02% | 100.12% | ND | 0.07% | 0.07% |
| | 12 | ✓ | 0.02% | 100.58% | ND | 0.03% | 0.03% |

Note:
[a]The appearance of the sample stayed as white or off-white crystalline powder.
[b]ND = not detected.

The test results showed that there are no apparent changes in the samples under the test conditions for up to 12 months. Therefore, it can be concluded that our product is stable under the long term stability test conditions for up to 12 months. The long term stability study is still on-going.

REFERENCES

The following references, to the extent that they provide exemplary procedural or other details supplementary to those set forth herein, are specifically incorporated herein by reference.
U.S. Pat. No. 4,024,175
U.S. Pat. No. 4,087,544
U.S. Pat. No. 5,091,567
U.S. Pat. No. 5,319,135
U.S. Pat. No. 6,054,482
U.S. Pat. No. 6,518,456
PCT Appln. WO 02/34709
PCT Appln. WO 2004046108
PCT Appln. WO 9914184
Indian Appln. 186285

What is claimed is:
1. A process for the preparation of highly pure, stable compound of formula

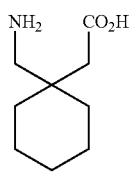

I comprising:
(a) converting cyclohexane 1,1-diacetic acid monoamide to 3,3-pentamethylenebutyrolactam by reacting cyclohexane 1,1-diacetic acid monoamide with hypochlorite;
(b) hydrolyzing 3,3-pentamethylenebutyrolactam to gabapentin salt under acidic condition at 50-120° C., cooling the reaction mixture to precipitate gabapentin salt, and collecting the gabapentin salt from the mother liquor by filtration;
(c) adding gabapentin salt to purified water and adjusting the pH to 8-8.5 with a base, cooling the mixture to 10-20° C. to precipitate gabapentin hydrate, and collecting the gabapentin hydrate from the mother liquor by filtration;
(d) dehydrating gabapentin hydrate in alcohol or water-alcohol solvent at below 50° C.; and
(e) collecting the pure gabapentin from the mother liquor by filtration; provided that process does not include ion exchange chromatography as a processing step.

2. The process according to claim 1, further comprising, following step (b) and prior to step (c), the steps of adding gabapentin salt to purified water, adjusting the pH with a base to pH=3-7 at −5 to 40° C., and removing impurity by stirring with activated carbon and silicate and subsequent filtration.

3. The process according to claim 1, wherein the reaction of step (a) further comprises:
(i) dissolving cyclohexane 1,1-diacetic acid monoamide (II) in a basic aqueous solution and adding the hypochlorite at below 50° C. to effect the reaction;
(ii) adding a reducing agent to destroy excess hypochlorite; and
(iii) adjusting the pH to 7-13 with an acid, and raising the temperature to 30-120° C. to effect the reaction to produce 3,3-pentamethylenebutyrolactam.

4. The process according to claim 3, wherein the basic aqueous solution of step (i) comprises alkaline metal hydroxide, carbonate, or combination thereof.

5. The process according to claim 4, wherein the basic aqueous solution of step (i) is NaOH or KOH or a combination thereof.

6. The process according to claim 5, wherein the concentration of the NaOH or KOH is 5 to 30%, and the molar ratio of NaOH or KOH to cyclohexane 1,1-diacetic acid monoamide is 2 to 10:1.

7. The process according to claim 3, wherein the hypochlorite of step (i) is NaClO, KClO, or Ca(ClO)$_2$ or combination thereof.

8. The process according to claim 7, wherein the hypochlorite is NaClO.

9. The process according to claim 3, wherein the chlorine content of the hypochlorite used in step (i) is 5 to 20% and the molar ratio of hypochlorite to cyclohexane 1,1-diacetic acid monoamide is 1 to 3:1.

10. The process according to claim 3, wherein the reducing agent of step (ii) is sodium sulfite or sodium bisulfite.

11. The process according to claim 3, wherein the acid in step (iii) is an inorganic acid or combination of inorganic acids.

12. The process according to claim 11, wherein the inorganic acid is HCl.

13. The process according to claim 3, wherein 3,3-pentamethylenebutyrolactam is isolated by extraction with a water-immiscible organic solvent or solvents.

14. The process according to claim 13, wherein the water-immiscible organic solvent is toluene or methylene chloride or combination thereof.

15. The process according to claim 3, wherein 3,3-pentamethylenebutyrolactam is isolated by filtration after the solution is concentrated and cooled or cooled directly.

16. The process according to claim 1, wherein the acid condition in step (b) comprises use of an inorganic acid.

17. The process according to claim 16, wherein the inorganic acid is hydrochloric acid, hydrobromic acid, sulfuric acid, or phosphoric acid, or combination thereof.

18. The process according to claim 16, wherein the molar ratio of the inorganic acid to 3,3-pentamethylenebutyrolactam is 2 to 15:1.

19. The process according to claim 1, wherein in step (c) the base used is alkaline metal hydroxide, carbonate, $NH_3$, or a combination thereof.

20. The process according to claim 19, wherein the alkaline metal hydroxide is NaOH or KOH or a combination thereof.

21. The process according to claim 1, wherein in step (c) the ratio of gabapentin salt to the weight of purified water is 1:0.5 to 5.

22. The process according to claim 1, wherein in step (d) the weight ratio of activated carbon to silicate is 1:0.1 to 5.

23. The process according to claim 1, wherein in step (e) the pH of the reaction mixture is adjusted with a base to pH=8-8.5 to precipitate gabapentin monohydrate.

24. The process according to claim 23, wherein the base used is alkaline metal hydroxide, carbonate, or combination thereof.

25. The process according to claim 24, wherein the base is NaOH or KOH or a combination thereof.

26. The process according to claim 1, wherein in step (f) the alcohol is $C_1$—$C_4$ alcohol or combination thereof.

27. The process according to claim 26, wherein the $C_1$—$C_4$ alcohol is ethanol.

28. The process according to claim 23, wherein the ratio of the weight of gabapentin monohydrate to that of alcohol is 1:0.5 to 5.

29. The process according to claim 1, wherein in step (f) the reaction temperature is between 0 to 50° C.

30. The process according to claim 1, further comprising adjusting the pH of the mother liquor of steps (b), (c) and/or (e) to between 8-14 with NaOH, heating the mother liquor or liquors at 60-120° C., and recovering 3,3-pentamethylenebutyrolactam.

31. The process according to claim 1, wherein the conversion of step (a) occurs at greater than about 95% yield.

* * * * *

UNITED STATES PATENT AND TRADEMARK OFFICE
CERTIFICATE OF CORRECTION

PATENT NO. : 7,442,834 B2  Page 1 of 1
APPLICATION NO. : 11/457023
DATED : October 28, 2008
INVENTOR(S) : Tianchun Liu et al.

It is certified that error appears in the above-identified patent and that said Letters Patent is hereby corrected as shown below:

In title page, item (30) Foreign Application Priority Data, insert:

--June 12, 2006 (CN) 200610051909.5
June 12, 2006 (CN) 200610051910.8--.

Signed and Sealed this

Twenty-seventh Day of January, 2009

JOHN DOLL
*Acting Director of the United States Patent and Trademark Office*